United States Patent
Liu et al.

(10) Patent No.: US 12,232,727 B2
(45) Date of Patent: Feb. 25, 2025

(54) ARTICULATING ENDOSCOPIC CUTTER STAPLER AND UNIVERSAL ASSEMBLY FOR STAPLING

(71) Applicant: Suzhou Meidong Huicheng Precision Components Co., Ltd., Jiangsu (CN)

(72) Inventors: Zide Liu, Jiangsu (CN); Lin Zhang, Jiangsu (CN); Zixian Liu, Jiangsu (CN); Shitao Ma, Jiangsu (CN); Qin Zhang, Jiangsu (CN)

(*) Notice: Subject to any disclaimer, the term of this patent is extended or adjusted under 35 U.S.C. 154(b) by 8 days.

(21) Appl. No.: 17/796,190

(22) PCT Filed: Nov. 9, 2021

(86) PCT No.: PCT/CN2021/129621
§ 371 (c)(1),
(2) Date: Jul. 28, 2022

(87) PCT Pub. No.: WO2023/065420
PCT Pub. Date: Apr. 27, 2023

(65) Prior Publication Data
US 2024/0180553 A1    Jun. 6, 2024

(30) Foreign Application Priority Data
Oct. 23, 2021    (CN) .......................... 202111236641.3

(51) Int. Cl.
| | | |
|---|---|---|
| *A61B 17/072* | (2006.01) | |
| *A61B 17/295* | (2006.01) | |
| *A61B 17/00* | (2006.01) | |

(52) U.S. Cl.
CPC ...... *A61B 17/07207* (2013.01); *A61B 17/295* (2013.01); *A61B 2017/00353* (2013.01);
(Continued)

(58) Field of Classification Search
CPC ............ A61B 17/07207; A61B 17/295; A61B 2017/00353; A61B 2017/00367; A61B 2017/07271; A61B 2017/07285
See application file for complete search history.

(56) References Cited

U.S. PATENT DOCUMENTS

| | | | | |
|---|---|---|---|---|
| 5,211,650 | A | * | 5/1993 | Noda .................. A61B 17/0469 606/147 |
| 2002/0082625 | A1 | * | 6/2002 | Huxel .................. A61B 17/115 606/153 |

(Continued)

FOREIGN PATENT DOCUMENTS

| | | | | |
|---|---|---|---|---|
| CN | 112515719 | * | 3/2021 | ......... A61B 17/0469 |
| CN | 113288270 | * | 8/2021 | ....... A61B 17/07207 |

(Continued)

*Primary Examiner* — Stephen F. Gerrity
*Assistant Examiner* — Linda J Hodge

(57) ABSTRACT

The present disclosure relates to the technical field of medical equipment, and discloses an articulating endoscopic cutter stapler and universal assembly for stapling, comprising a proper, wherein the surface of the proper is slidably connected with a reset ring and formed with a slot, the surface of the reset ring is provided with a sliding pin which is placed into the slot, and a safety pin is arranged at one end of the surface of the proper. The present disclosure can better control the anvil assembly to improve the stability of stapler during suturing of wound and to improve the quality of surgical suturing. The angle of suturing assembly of stapler can also be adjusted to the specific position of the wound, so that the range of application of stapler can be extended.

8 Claims, 7 Drawing Sheets

(52) U.S. Cl.
CPC ............... *A61B 2017/00367* (2013.01); *A61B 2017/07271* (2013.01); *A61B 2017/07285* (2013.01)

(56) References Cited

U.S. PATENT DOCUMENTS

2018/0132847 A1* 5/2018 Kostrzewski ........ A61B 17/105
2020/0093486 A1* 3/2020 Somekh ............... A61B 17/068

FOREIGN PATENT DOCUMENTS

| CN | 113509230 | * | 10/2021 | ....... A61B 17/07207 |
| WO | WO-2009117533 A2 | * | 9/2009 | ....... A61B 17/00234 |

* cited by examiner

ARTICULATING ENDOSCOPIC CUTTER STAPLER AND UNIVERSAL ASSEMBLY FOR STAPLING

TECHNICAL FIELD

The present disclosure relates to the technical field of medical equipment, and discloses an articulating endoscopic cutter stapler and universal assembly for stapling.

BACKGROUND

Driven by the increasing demands on concept of "minimally-invasive deft treatment" in recent years, surgical departments from major hospitals of China have successively carried out total-laparoscopic radical gastrectomy, which has been highly valued and concerned by doctors from minimally-invasive surgical departments. However, as for China, total-laparoscopic radical gastrectomy is still in its stage of preliminary exploration as it has only been carried out for a shorter time period. It is still uncertain that whether the total-laparoscopic radical gastrectomy can reach a surgical safety and feasibility as well as short- and long-term efficacies equivalent to those realized by traditional partial-laparoscopic surgery, and can practically reduce surgical injuries, speed up postoperative recovery and reduce disturbance to original appearances of internal organs. As the first suturing instrument used all over the world, stapler is of a medical instrument to replace the manual suturing operation, wherein it operates under the main principle that tissues are dissociated or stapled by titanium nails (similar to a book stapler). In comparison to the traditional manual suturing operation, stapler is more convenient to operate with a better effect of suturing.

For use of a stapler at present, generally it is required to suture wounds in different positions, and therefore to change the angle of the stapler. However, with a general stapler, in the course of suturing, it is not convenient to change the angle of the already-assembled stapler to adapt to wounds in different positions, but it is required to disassemble and then install again the stapler to achieve this purpose, which may make the stapler impractical and lower the efficiency in surgical operation for the wound. Moreover, it is not convenient to connect and install components inside the general stapler as there is a complex structure in this regard, which may easily bring about a failure in stapler. In this case, any delay in handling this kind of failure may result in an improper control and operation of the stapler, which may affect the effect of suturing realized by the stapler, and therefore make the stapler impractical.

SUMMARY

The present disclosure provides an articulating endoscopic cutter stapler and universal assembly for stapling, featuring a convenience in changing the angle of stapler to adapt to wounds in different positions, and a feasibility of assembling for components of the stapler, thereby solving the issues mentioned in said background above.

To realize this purpose, the present disclosure provides the following technical solutions: an articulating endoscopic cutter stapler and universal assembly for stapling, comprising a proper, wherein the surface of the proper is slidably connected with a reset ring and formed with a slot, the surface of the reset ring is provided with a sliding pin which is placed into the slot, a safety pin is arranged at one end of the surface of the proper, a connector is fixedly connected with one end of the proper, the surface of the connector is provided with a fastener to facilitate removal, an endoscopic duct is installed inside the connector, a turning handle is installed in a penetrating manner inside the proper, one end of the turning handle is in a transmission connection with the endoscopic duct, a fixing handle is fixedly connected with the bottom of the proper, a rotating shaft is provided inside the proper, a closing handle is fixedly connected to the bottom surface of the rotating shaft, one end of the closing handle penetrates to the surface of the proper, the closing handle is installed inside the proper, a connecting rod is fixedly connected with the surface of the closing handle, a control assembly is fixedly connected with one end of the connecting rod far away from the closing handle, a compression bar is fixedly connected with the top surface of the rotating shaft, a push rod is installed inside the endoscopic duct and fitted with the compression bar, a slide carriage is installed inside the endoscopic duct, adjustable springs are installed on the surfaces at both ends of the slide carriage, sliding blocks are fixedly connected with the ends of the adjustable springs far away from the slide carriage, the bottoms of the sliding blocks are connected with the surface of the slide carriage in a sliding manner while the tops thereof are fixedly connected with the push rod, an installation tubing is installed at one end of the endoscopic duct, a turning connector plate is fixedly connected with the surface at one end of the installation tubing, a cartridge ejector is installed at one end of the installation tubing, one end of the cartridge ejector is connected rotatably with the turning connector plate, an adjusting panel is arranged on the surface of the connector in a penetrating manner and fitted with the cartridge ejector, an ejector plate fitted with the push rod is connected in a sliding manner inside the cartridge ejector, racks are formed on the surface of the ejector plate, a runner is installed inside the cartridge ejector, the surface of the runner is engaged with the surfaces of the racks, an anvil assembly is fixedly connected with the surface of the runner, and a cartridge is installed inside the cartridge ejector.

As the articulating endoscopic cutter stapler and universal assembly for stapling in the present disclosure, said control assembly comprises a sleeve, a return spring, a stop slider, a stop sliding tube, a stop slip and an ejector sleeve, wherein the sleeve is fixedly connected inside the proper, the return spring is installed inside the sleeve, the stop slider is connected in a sliding manner inside the sleeve, the stop sliding tube is connected in a sliding manner on the surface of the stop slider, the toothed plate on surface of the stop slider is fitted with the tooth-shaped slot on surface of the stop sliding tube, the ejector sleeve is installed inside the stop sliding tube, the stop slip is installed on the surface of the ejector sleeve, the stop slip is connected with the stop sliding tube in a sliding manner, the teeth on the stop slider are fitted with the tooth-shaped slot on the ejector sleeve, and one end of the ejector sleeve is fixedly connected with the connecting rod.

As the articulating endoscopic cutter stapler and universal assembly for stapling in the present disclosure, an installation joint is fixedly connected with the top of the installation tubing, multiple clamping blocks are installed on the surface and placed in different positions of the installation joint, the installation joint is clamped with the endoscopic duct, and the endoscopic duct is fitted with the fastener to facilitate removal.

As the articulating endoscopic cutter stapler and universal assembly for stapling in the present disclosure, two installation insert blocks are fixedly connected with one end of the cartridge, square slots are formed on the surfaces of the installation insert blocks, notches are formed inside the square slots, two compression springs are installed inside the notches, stop blocks are formed on surfaces of the installation insert blocks and placed into the square slots, bulges are formed on surfaces of the stop blocks and placed into the notches, one side of each of the bulges is fixedly connected with one end of each of the compression springs, a button to facilitate removal is installed on surface of the cartridge ejector and fitted with the stop blocks.

As the articulating endoscopic cutter stapler and universal assembly for stapling in the present disclosure, a cutting slot is formed on surface of the cartridge, a cutter is connected in a sliding manner on the surface of the cartridge and placed into the cutting slot, one end of the cutter is cambered, and the cutter is in the same width as the cutting slot.

As the articulating endoscopic cutter stapler and universal assembly for stapling in the present disclosure, several ejector slots are formed on the surface of the cartridge and placed symmetrically on both sides of the cutting slot, and suturing nails are provided inside the ejector slots.

As the articulating endoscopic cutter stapler and universal assembly for stapling in the present disclosure, a buckle plate is fixedly connected with the top surface of the reset ring, the buckle plate is made of rigid plastic materials, and the surface on one side of the buckle plate is concavely cambered.

As the articulating endoscopic cutter stapler and universal assembly for stapling in the present disclosure, a rubber protective coat is provided on the surface of the fixing handle, wave-like skid-proof stripes are formed on the surface of the closing handle, and uniformly spaced stripes are formed on the surface of turning handle.

The present disclosure provides an articulating endoscopic cutter stapler and universal assembly for stapling, with the following beneficial effects:

(1) The articulating endoscopic cutter stapler and universal assembly for stapling in the present disclosure, wherein with the designs for proper, fixing handle, closing handle, rotating shaft, compression bar, push rod, ejector plate, anvil assembly, slide carriage, adjustable springs, sliding blocks, runner, connecting rod, control assembly and racks, the anvil assembly can be better controlled, to improve the stability of stapler during suturing of wound and to improve the quality of surgical suturing; with the designs for adjusting panel, installation tubing, turning connector plate and cartridge ejector, the angle of suturing assembly of stapler can be adjusted to the specific position of the wound, so that the range of application of stapler can be extended; with the designs for turning handle and endoscopic duct, suturing assembly of stapler can be turned conveniently to adapt to the specific position of the wound; and with the designs for safety pin, reset ring, slot and sliding pin, the depth of cutting by cutter in the wound can be controlled as the case may be, so that the surgical effect can be improved.

(2) The articulating endoscopic cutter stapler and universal assembly for stapling in the present disclosure, wherein with the designs for installation joint, clamping blocks, installation tubing and fastener to facilitate removal, suturing assembly can be installed at the endoscopic duct in a more convenient manner and then the installation tubing can be stopped and fixed, so that the stability of connection between installation tubing and endoscopic duct can be improved and the effect of operating the stapler can be improved; and with the designs for installation insert blocks, square slots, notches, compression springs, stop blocks, bulges and button to facilitate removal, cartridge can be conveniently replaced and installed as per the specific state of the wound, so that the stapler is more practical, to shorten the work time and improve the surgical efficiency.

In these FIGs, 1—proper; 2—reset ring; 3—buckle plate; 4—safety pin; 5—fixing handle; 6—closing handle; 7—turning handle; 8—slot; 9—sliding pin; 10—connector; 11—adjusting panel; 12—fastener to facilitate removal; 13—endoscopic duct; 14—installation tubing; 15—turning connector plate; 16—cartridge; 17—anvil assembly; 18—cutting slot; 19—cutter; 20—ejector slot; 21—push rod; 22—slide carriage; 23—installation joint; 24—clamping blocks; 25—ejector plate; 26—compression bar; 27—rotating shaft; 28—connecting rod; 29—control assembly; 2901—sleeve; 2902—return spring; 2903—stop slider; 2904—stop sliding tube; 2905—stop slip; 2906—ejector sleeve; 30—installation insert blocks; 31—adjustable springs; 32—sliding blocks; 33—runner; 34—racks; 35—square slots; 36—notches; 37—compression springs; 38—stop blocks; 39—bugles; 40—button to facilitate removal; 41—cartridge ejector.

DETAILED DESCRIPTION

Technical solutions in embodiments of the present disclosure will be clearly and completely described with reference to the figures in the embodiments of the present disclosure. Apparently, the embodiments described below are merely part, not all, of the embodiments of the present disclosure. Based on the embodiments described herein, all other embodiments obtained by those of ordinary skill in the art without creative work are within the scope of the present disclosure.

It should be noted in description of the present disclosure that the directions or position relationships such as "upper", "lower", "inside", "outside" and "top/bottom" are based on those shown in the figures, and are used only for facilitating the description of the present disclosure and for simplified description, not for indicating or implying that the target devices or components must have a special direction and be structured and operated at the special direction, therefore they cannot be understood as the restrictions to the present disclosure. Moreover, the words "first" and "second" are used only for description, and cannot be understood as an indication or implication of relative importance.

It should be noted in the description of the present disclosure that unless otherwise specified or restricted, the words of "installation", "provided with", "sleeved/connected with" and "connection" should be understood as a general sense. For example, the "connection" can be fixed connection, removable connection, integrated connection, mechanical connection, electrical connection, direct connection, indirect connection through intermediate media or connection between two components. Persons of ordinary skill in the art can understand the specific meanings of the terms above in the present disclosure as the case may be.

Figure 1:
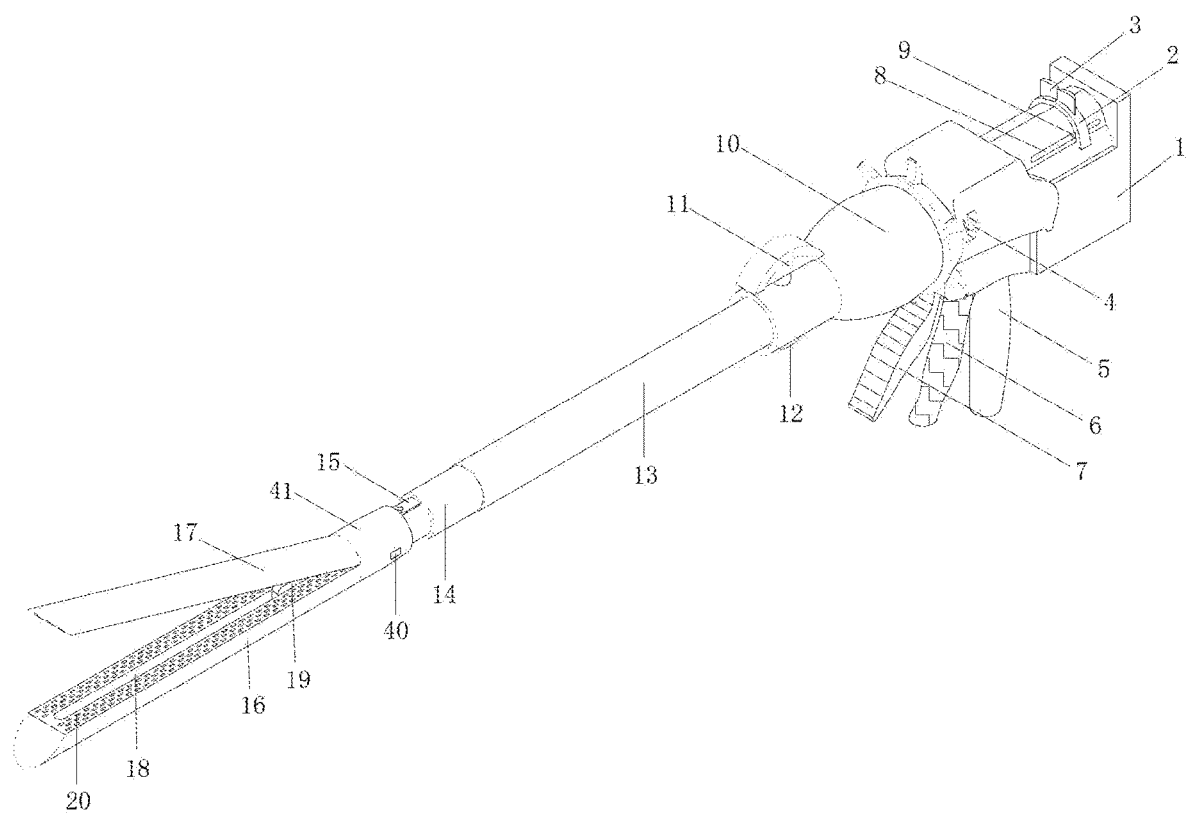
FIG. 1 is the three-dimensional view of the present disclosure.
Figure 2:
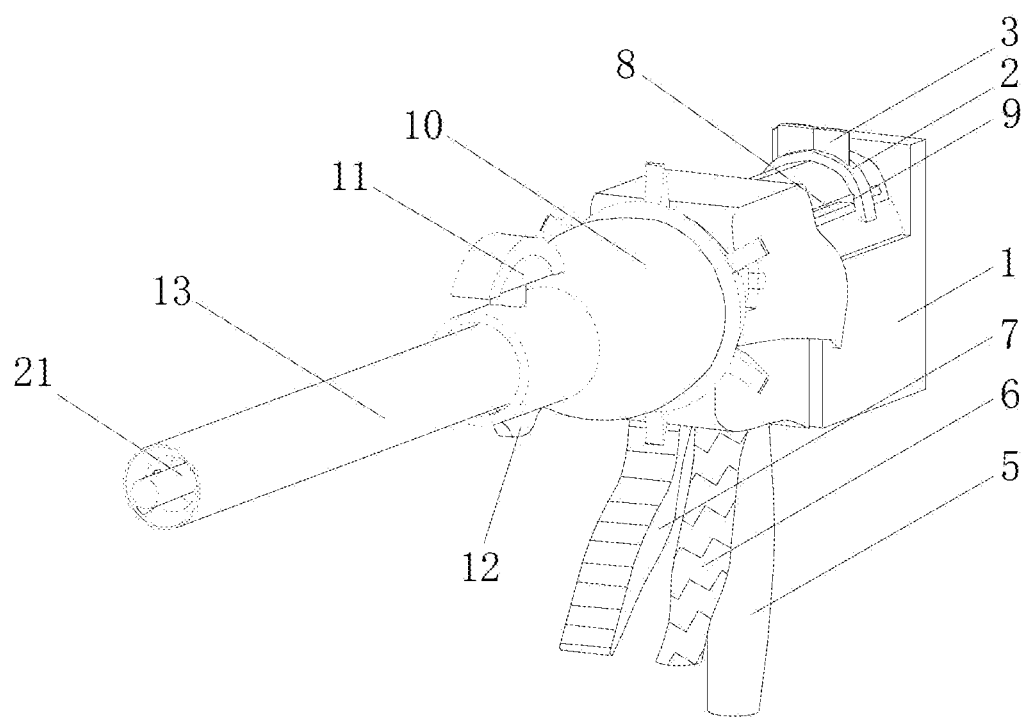
FIG. 2 is the three-dimensional view for local structure of the present disclosure.
Figure 3:
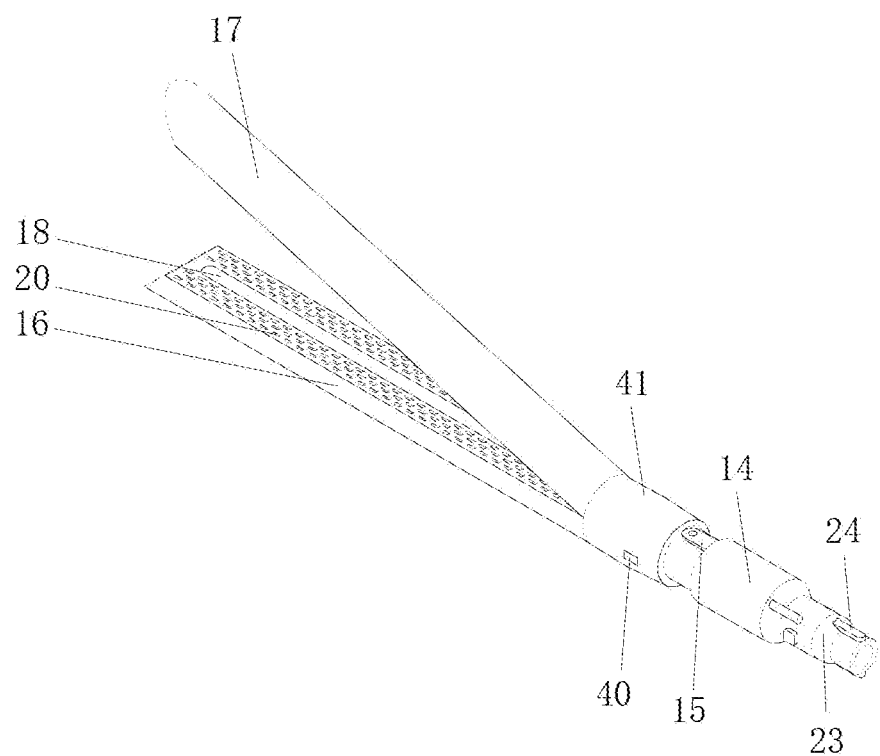
FIG. 3 is the three-dimensional view for local structure of the present disclosure.
Figure 4:
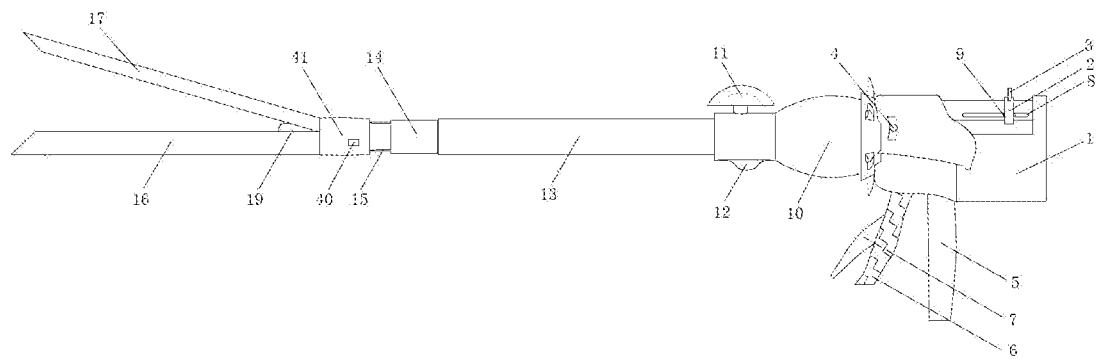
FIG. 4 is the side view of the present disclosure.
Figure 5:
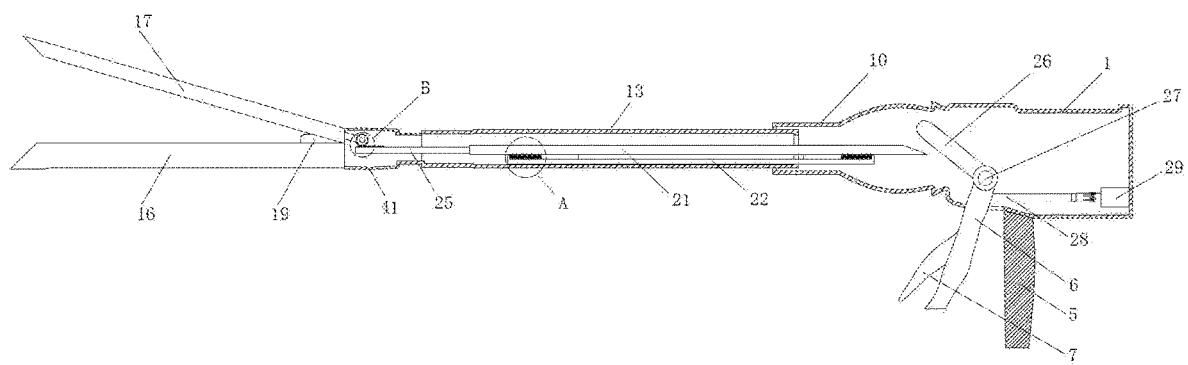
FIG. 5 is the cross-sectional view for local structure of the present disclosure.
Figure 6:
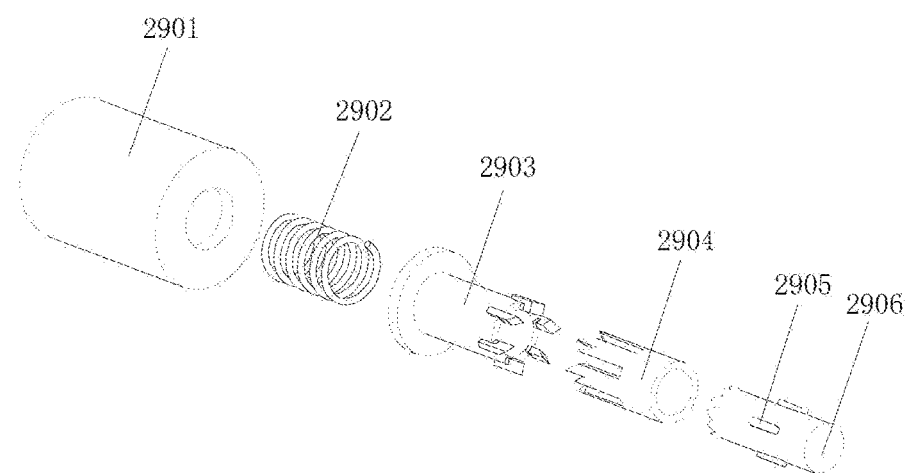
FIG. 6 is the exploded view for local structure of the present disclosure.
Figure 7:
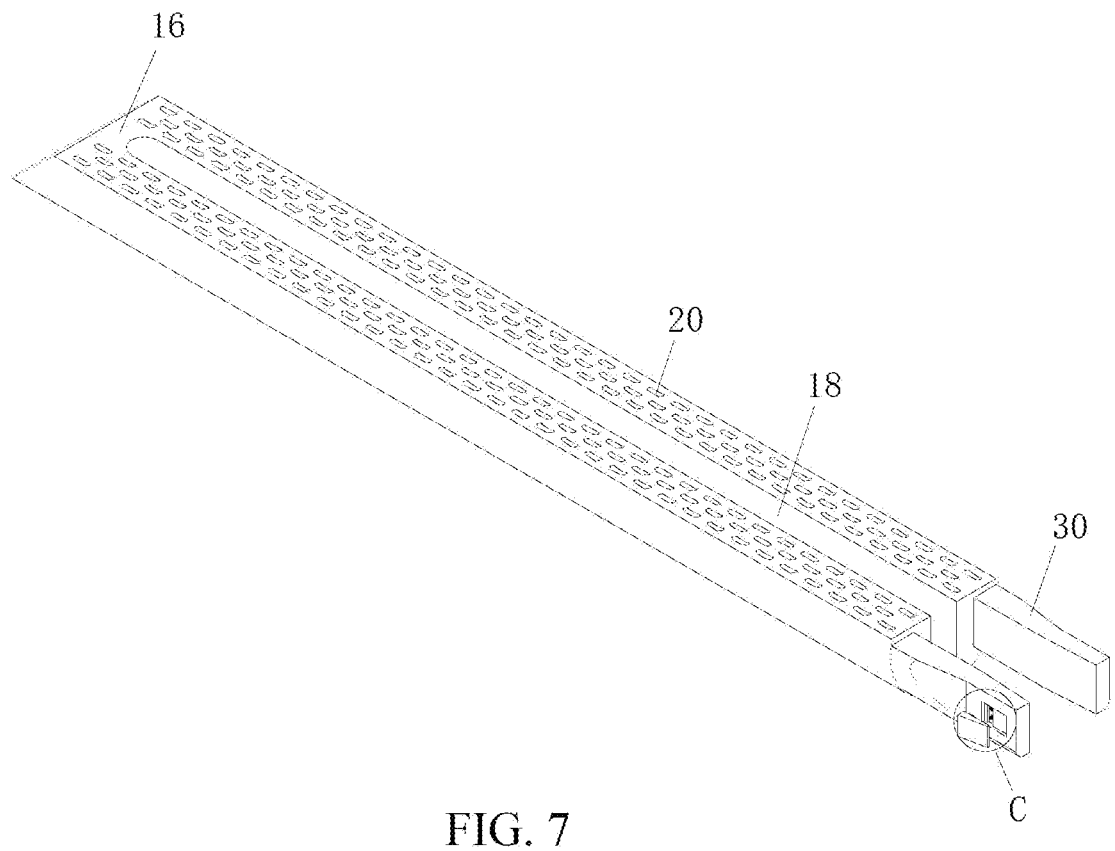
FIG. 7 is the three-dimensional view for local structure of the present disclosure.
Figure 8:
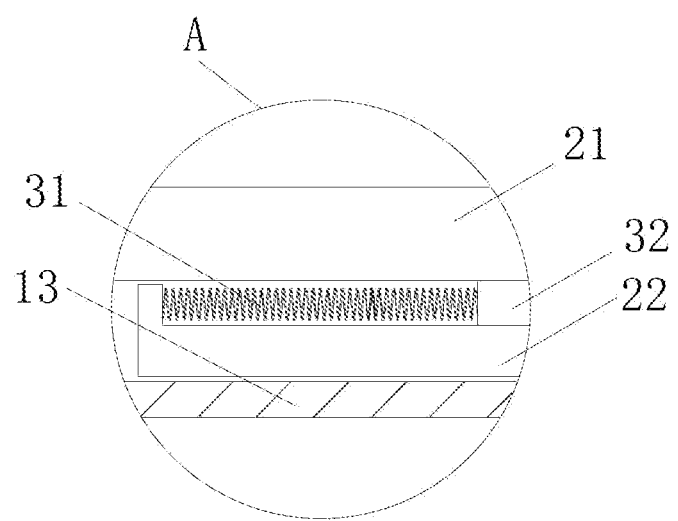
FIG. 8 is the enlarged view for structure A as shown in FIG. 5 of the present disclosure.
Figure 9:
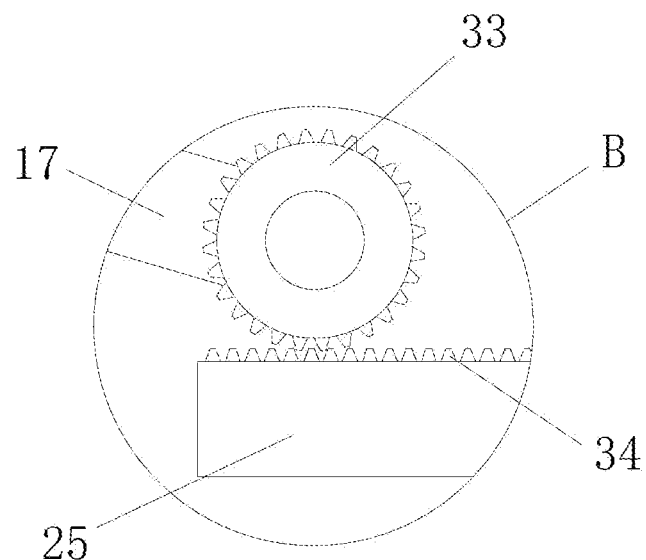
FIG. 9 is the enlarged view for structure B as shown in FIG. 5 of the present disclosure.
Figure 10:
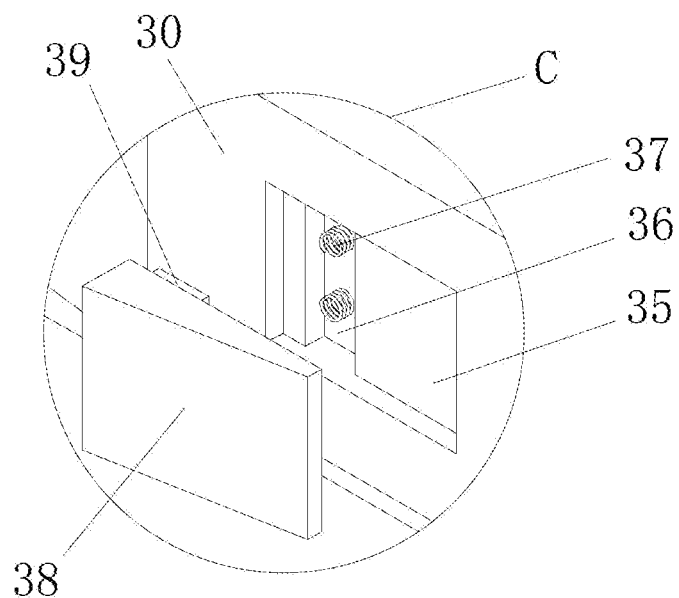
FIG. 10 is the enlarged view for structure C as shown in FIG. 7 of the present disclosure.

As shown in FIG. 1-10, the present disclosure provides a technical solution, comprising a proper 1, wherein the surface of the proper 1 is slidably connected with a reset ring 2 and formed with a slot 8, the surface of the reset ring 2 is provided with a sliding pin 9 which is placed into the slot 8, a safety pin 4 is arranged at one end of the surface of the proper 1, a connector 10 is fixedly connected with one end of the proper 1, the surface of the connector 10 is provided with a fastener 12 to facilitate removal, an endoscopic duct 13 is installed inside the connector 10, a turning handle 7 is installed in a penetrating manner inside the proper 1, one end of the turning handle 7 is in a transmission connection with the endoscopic duct 13, a fixing handle 5 is fixedly connected with the bottom of the proper 1, a rotating shaft 27 is provided inside the proper 1, a closing handle 6 is fixedly connected to the bottom surface of the rotating shaft 27, one end of the closing handle 6 penetrates to the surface of the proper 1, the closing handle 6 is installed inside the proper 1, a connecting rod 28 is fixedly connected with the surface of the closing handle 6, a control assembly 29 is fixedly connected with one end of the connecting rod 28 far away from the closing handle 6, a compression bar 26 is fixedly connected with the top surface of the rotating shaft 27, a push rod 21 is installed inside the endoscopic duct 13 and fitted with the compression bar 26, a slide carriage 22 is installed inside the endoscopic duct 13, adjustable springs 31 are installed on the surfaces at both ends of the slide carriage 22, sliding blocks 32 are fixedly connected with the ends of the adjustable springs 31 far away from the slide carriage 22, the bottoms of the sliding blocks 32 are connected with the surface of the slide carriage 22 in a sliding manner while the tops thereof are fixedly connected with the push rod 21, an installation tubing 14 is installed at one end of the endoscopic duct 13, a turning connector plate 15 is fixedly connected with the surface at one end of the installation tubing 14, a cartridge ejector 41 is installed at one end of the installation tubing 14, one end of the cartridge ejector 41 is connected rotatably with the turning connector plate 15, an adjusting panel 11 is arranged on the surface of the connector 10 in a penetrating manner and fitted with the cartridge ejector 41, an ejector plate 25 fitted with the push rod 21 is connected in a sliding manner inside the cartridge ejector 41, racks 34 are formed on the surface of the ejector plate 25, a runner 33 is installed inside the cartridge ejector 41, the surface of the runner 33 is engaged with the surfaces of the racks 34, an anvil assembly 17 is fixedly connected with the surface of the runner 33, and a cartridge 16 is installed inside the cartridge ejector 41.

In this embodiment, with the designs for proper 1, reset ring 2, slot 8, safety pin 4, connector 10, fastener 12 to facilitate removal, endoscopic duct 13, turning handle 7, fixing handle 5, rotating shaft 27, closing handle 6, connecting rod 28, control assembly 29, compression bar 26, push rod 21, slide carriage 22, adjustable springs 31, sliding blocks 32, installation tubing 14, cartridge ejector 41, turning connector plate 15, adjusting panel 11, ejector plate 25, racks 34, runner 33, anvil assembly 17 and cartridge 16, components of the stapler can be installed and used conveniently, to reduce errors in surgical operation due to improper operation of the stapler and therefore improve the effect of suturing after the surgery, and moreover upon installation of components for stapler, angle of the stapler can be conveniently adjusted to adapt to the specific position of the wound, so that the stapler is more practical with a higher efficiency of suturing for the wound.

Specifically, the control assembly 29 comprises a sleeve 2901, a return spring 2902, a stop slider 2903, a stop sliding tube 2904, a stop slip 2905 and an ejector sleeve 2906, wherein the sleeve 2901 is fixedly connected inside the proper 1, the return spring 2902 is installed inside the sleeve 2901, the stop slider 2903 is connected in a sliding manner inside the sleeve 2901, the stop sliding tube 2904 is connected in a sliding manner on the surface of the stop slider 2903, the toothed plate on surface of the stop slider 2903 is fitted with the tooth-shaped slot on surface of the stop sliding tube 2904, the ejector sleeve 2906 is installed inside the stop sliding tube 2904, the stop slip 2905 is installed on the surface of the ejector sleeve 2906, the stop slip 2905 is connected with the stop sliding tube 2904 in a sliding manner, the teeth on the stop slider 2903 are fitted with the tooth-shaped slot on the ejector sleeve 2906, and one end of the ejector sleeve 2906 is fixedly connected with the connecting rod 28.

In this embodiment, with the designs for sleeve 2901, return spring 2902, stop slider 2903, stop sliding tube 2904, stop slip 2905 and ejector sleeve 2906, the closing handle 6 can be controlled conveniently to better control the closing for anvil assembly 17, thereby realizing a higher control strength of stapler in the course of a surgery.

Specifically, an installation joint 23 is fixedly connected with the top of the installation tubing 14, multiple clamping blocks 24 are installed on the surface and placed in different positions of the installation joint 23, the installation joint 23 is clamped with the endoscopic duct 13, and the endoscopic duct 13 is fitted with the fastener 12 to facilitate removal.

In this embodiment, with the designs for installation joint 23 and clamping blocks 24, the installation tubing 14 can be conveniently installed and clamped with the endoscopic duct 13, to improve the efficiency of assembling and disassembling the components for installation tubing 14 and therefore save the work time.

Specifically, two installation insert blocks 30 are fixedly connected with one end of the cartridge 16, square slots 35 are formed on the surfaces of the installation insert blocks 30, notches 36 are formed inside the square slots 35, two compression springs 37 are installed inside the notches 36, stop blocks 38 are formed on surfaces of the installation insert blocks 30 and placed into the square slots 35, bulges 39 are formed on surfaces of the stop blocks 38 and placed into the notches 36, one side of each of the bulges 39 is fixedly connected with one end of each of the compression springs 37, a button 40 to facilitate removal is installed on surface of the cartridge ejector 41 and fitted with the stop blocks 38.

In this embodiment, with the designs for installation insert blocks 30, square slots 35, notches 36, compression springs 37, stop blocks 38, bulges 39, cartridge ejector 41 and button 40 to facilitate removal, the cartridge 16 and cartridge ejector 41 can be conveniently installed and cartridge 16 can be replaced conveniently for suturing of wounds in different positions, so that the range of application of stapler can be extended with a higher efficiency of suturing in a surgery.

Specifically, a cutting slot 18 is formed on surface of the cartridge 16, a cutter 19 is connected in a sliding manner on the surface of the cartridge 16 and placed into the cutting slot 18, one end of the cutter 19 is cambered, and the cutter 19 is in the same width as the cutting slot 18.

In this embodiment, with the designs for the cutting slot 18 and the cutter 19, precise cutting at the wound can be realized, to avoid any deviation in cutting which may result in a poor effect of suturing and aggravate the pain.

Specifically, several ejector slots 20 are formed on the surface of the cartridge 16 and placed symmetrically on both sides of the cutting slot 18, and suturing nails are provided inside the ejector slots 20.

In this embodiment, with the design for ejector slots 20, a neat effect of suturing can be realized at the wound, to prevent poor tightness on two sides of the sutured wound (poor effect of suturing).

Specifically, a buckle plate 3 is fixedly connected with the top surface of the reset ring 2, the buckle plate 3 is made of rigid plastic materials, and the surface on one side of the buckle plate 3 is concavely cambered.

In this embodiment, with the design for buckle plate 3, the buckle plate 3 can be moved and returned to its original position conveniently upon the suturing, to drive the cutter 19 to return its original position.

Specifically, a rubber protective coat is provided on the surface of the fixing handle 5, wave-like skid-proof stripes are formed on the surface of the closing handle 6, and uniformly spaced stripes are formed on the surface of turning handle 7.

In this embodiment, with the designs for protective coat provided on surface of the fixing handle 5, skid-proof stripes formed on surface of closing handle 6 and stripes formed on surface of turning handle 7, stapler can be held and operated more steadily by a user, and is therefore more practical during a surgery.

Use of the stapler: First of all, align and insert installation joint 23 connected with installation tubing 14 in suturing assembly into endoscopic duct 13, in this case the clamping blocks 24 on surface of the installation joint 23 are placed into the endoscopic duct 13; once the installation joint 23 is fully inserted into the endoscopic duct 13, turn the installation joint 23 in a clockwise direction, in this case the clamping blocks 24 are clamped with limit stops in the endoscopic duct 13; slide the fastener 12 to facilitate removal towards the surface of the connector 10 and fasten it, and then select an appropriate cartridge 16 as per the specific state of the wound; insert the installation insert blocks 30 on the cartridge 16 into the cartridge ejector 41 for installation and fixing until the stop blocks 38 are compressed, and slide towards the inside of the square slots 35 until the compression springs 37 are compressed by bulges 39; once the stop blocks 38 are moved to the position corresponding to button 40 to facilitate removal in the cartridge ejector 41, stop blocks 38 can be ejected out by reacting force of the compression springs 37 to realize the function of limit stop, and in the course of suturing, control the closing handle 6 to drive the compression bar 26 to rotate; afterwards, use the compression bar 26 to drive the slide carriage 22 to move so that the push rod 21 can drive the sliding blocks 32 to slide on the slide carriage 22, in this case adjustable springs 31 are driven by the pressure applied from the sliding blocks 32 to move; use the push rod 21 to drive the ejector plate 25 to move and use the racks 34 on the surface of the ejector plate 25 to drive the runner 33 to rotate; switch the anvil assembly 17; as per actual needs in a surgery, turn the adjusting panel 11 to set the horizontal angle of cartridge ejector 41 to 45°, and then hold the turning handle 7 to drive the endoscopic duct 13 to rotate if necessary, so that the overall angle of the stapler can be adjusted until an alignment of the stapler to the wound; once the stapler is clamped at the wound, press down the safety pin 4 and control the cutter 19 to cut in a sliding manner in the cutting slot 18, in this case reset ring 2 will slide in the slot 8 together with the sliding of the cutter 19; once the cutting is done, suturing nails inside the ejector slots 20 are clamped with the anvil assembly 17 to suture the wound; once the suturing of the wound is done, use buckle plate 3 to return the reset ring 2 to its original position, use reset ring 2 to return the cutter 19 to its original position, and then remove the stapler from the wound.

The foregoing description is just the detailed description of the preferred embodiments to which, however, the protection scope in the present disclosure is not limited. Alternatives or variations made in accordance with technical solutions and new concepts of the present disclosure by any technicians familiar with the field of the present disclosure within the technical field disclosed in the present disclosure shall be also covered by the protection scope of the present disclosure.

What is claimed is:

1. An articulating endoscopic cutter stapler and universal assembly for stapling, comprising a stapler body, wherein a surface of the stapler body is slidably connected with a reset ring, the surface of the stapler body is equipped with a slot, a surface of the reset ring is provided with a sliding pin which is placed into the slot, a safety pin is arranged at one end of the surface of the stapler body, a connector is fixedly connected with one end of the stapler body, a surface of the connector is provided with a removal fastener, an endoscopic duct is installed inside the connector, a turning handle is installed in a penetrating manner inside the stapler body, one end of the turning handle is in a transmission connection with the endoscopic duct, a fixing handle is fixedly connected with a bottom of the stapler body, a rotating shaft is provided inside the staple body, a closing handle is fixedly connected to the bottom surface of the rotating shaft, one end of the closing handle penetrates to the surface of the stapler body, the closing handle is installed inside the stapler body, a connecting rod is fixedly connected with a surface of the closing handle, a control assembly is fixedly connected with one end of the connecting rod far away from the closing handle, a compression bar is fixedly connected with a top surface of the rotating shaft, a push rod is installed inside the endoscopic duct and fitted with the compression bar, a slide carriage is installed inside the endoscopic duct, adjustable springs are installed on surfaces at both ends of the slide carriage, sliding blocks are fixedly connected with the ends of the adjustable springs far away from the slide carriage, bottoms of the sliding blocks are connected with the surface of the slide carriage in a sliding manner while tops thereof are fixedly connected with the push rod, an installation tubing is installed at one end of the endoscopic duct, a turning connector plate is fixedly connected with a surface at one end of the installation tubing, a cartridge ejector is installed at the one end of the installation tubing, one end of the cartridge ejector is connected rotatably with the turning connector plate, an adjusting panel is arranged on the surface of the connector in a penetrating manner and fitted with the cartridge ejector, an ejector plate fitted with the push rod is connected in a sliding manner inside the cartridge ejector, racks are formed on a surface of the ejector plate, a runner is installed inside the cartridge ejector, a surface of the runner is engaged with surfaces of the racks, an anvil assembly is fixedly connected with the surface of the runner, and a cartridge is installed inside the cartridge ejector.

2. The articulating endoscopic cutter stapler and universal assembly for stapling according to claim 1, wherein said control assembly comprises a sleeve, a return spring, a stop slider, a stop sliding tube, a stop slip, and an ejector sleeve; the sleeve is fixedly connected inside the stapler body, the return spring is installed inside the sleeve, the stop slider is connected in a sliding manner inside the sleeve, the stop sliding tube is connected in a sliding manner on a surface of the stop slider, a toothed plate on the surface of the stop slider is fitted with a tooth-shaped slot on a surface of the stop sliding tube, the ejector sleeve is installed inside the stop sliding tube, the stop slip is installed on a surface of the ejector sleeve, the stop slip is connected with the stop sliding tube in a sliding manner, teeth on the stop slider are fitted with the tooth-shaped slot on the ejector sleeve, and one end of the ejector sleeve is fixedly connected with the connecting rod.

3. The articulating endoscopic cutter stapler and universal assembly for stapling according to claim 1, wherein an installation joint is fixedly connected with a top of the installation tubing, multiple clamping blocks are installed on a surface and placed in different positions of the installation joint, the installation joint is clamped with the endoscopic duct, and the endoscopic duct is fitted with the removal fastener.

4. The articulating endoscopic cutter stapler and universal assembly for stapling according to claim 1, wherein two installation insert blocks are fixedly connected with one end of the cartridge, square slots are formed on surfaces of the installation insert blocks, notches are formed inside the square slots, two compression springs are installed inside the notches, stop blocks are formed on surfaces of the installation insert blocks and placed into the square slots, bulges are formed on surfaces of the stop blocks and placed into the notches, one side of each of the bulges is fixedly connected with one end of each of the compression springs, a removal button is installed on a surface of the cartridge ejector and fitted with the stop blocks.

5. The articulating endoscopic cutter stapler and universal assembly for stapling according to claim 4, wherein a buckle plate is fixedly connected with a top surface of the reset ring, the buckle plate is made of rigid plastic materials, and a surface on one side of the buckle plate is concavely cambered.

6. The articulating endoscopic cutter stapler and universal assembly for stapling according to claim 1, wherein a cutting slot is formed on a surface of the cartridge, a cutter is connected in a sliding manner on the surface of the cartridge and placed into the cutting slot, one end of the cutter is cambered, and the cutter is in a same width as the cutting slot.

7. The articulating endoscopic cutter stapler and universal assembly for stapling according to claim 1, wherein several ejector slots are formed on the surface of the cartridge and placed symmetrically on both sides of a cutting slot and suturing nails are provided inside the ejector slots.

8. The articulating endoscopic cutter stapler and universal assembly for stapling according to claim 1, wherein a rubber protective coat is provided on a surface of the fixing handle, skid-proof stripes are formed on a surface of the closing handle, and uniformly spaced stripes are formed on a surface of the turning handle.

* * * * *